(12) United States Patent
Yu et al.

(10) Patent No.: US 10,473,951 B2
(45) Date of Patent: Nov. 12, 2019

(54) METHOD AND SYSTEM FOR DETERMINING PERSONALIZED NEAR ADDITION VALUE, LENS WITH SUCH ADDITION

(71) Applicant: Essilor International, Charenton-le-Pont (FR)

(72) Inventors: XinPing Yu, Wenzhou (CN); Jinhua Bao, Wenzhou (CN); Björn Drobe, Wenzhou (CN); Wenhui Lv, Wenzhou (CN); Hao Chen, Wenzhou (CN); Jinling Xu, Wenzhou (CN); Ge Wu, Wenzhou (CN)

(73) Assignee: Essilor International, Charenton-le-Pont (FR)

( * ) Notice: Subject to any disclaimer, the term of this patent is extended or adjusted under 35 U.S.C. 154(b) by 0 days.

(21) Appl. No.: 15/123,945

(22) PCT Filed: Mar. 7, 2014

(86) PCT No.: PCT/CN2014/073061
§ 371 (c)(1),
(2) Date: Sep. 6, 2016

(87) PCT Pub. No.: WO2015/131399
PCT Pub. Date: Sep. 11, 2015

(65) Prior Publication Data
US 2017/0023798 A1    Jan. 26, 2017

(51) Int. Cl.
*G02C 7/02* (2006.01)
*A61B 3/103* (2006.01)
(Continued)

(52) U.S. Cl.
CPC .......... *G02C 7/027* (2013.01); *A61B 3/0025* (2013.01); *A61B 3/028* (2013.01); *A61B 3/08* (2013.01);
(Continued)

(58) Field of Classification Search
CPC .......... A61B 3/103; A61B 3/028; A61B 3/08; A61B 3/0025; A61B 3/09; A61B 3/113;
(Continued)

(56) References Cited

U.S. PATENT DOCUMENTS 8,511,819 B2    8/2013  Reis
2012/0092621 A1*  4/2012  Ozaki ............... A61B 3/028
                                              351/234

FOREIGN PATENT DOCUMENTS

CN    102369476    3/2012
CN    102804029    11/2012

OTHER PUBLICATIONS

Toole et al, "Symptoms and Their Relationship to Positive Fusional Vergence and the Positive Fusional Vergence/Phoria Ratio: The CITT Pilot Study", ARVO Annual Meeting Abstract | May 2006; Investigative Ophthalmology & Visual Science May 2006, vol. 47 (13), 3143.*

(Continued)

*Primary Examiner* — Jie Lei
(74) *Attorney, Agent, or Firm* — Oblon, McClelland, Maier & Neustadt, L.L.P.

(57) ABSTRACT

A method for determining personalized near addition value for non-presbyopes, including measuring fusional amplitudes and phoria with at least one addition value, on both eyes of a person at a working distance; finding a mathematical function that predicts the change of a pair of fusional amplitudes and phoria as a function of addition value based on the addition value and the measured fusional amplitudes (Continued)

and phoria; and determining the near addition value according to a suitable relationship between the pair of fusional amplitudes and phoria on the mathematical function.

15 Claims, 6 Drawing Sheets (51) Int. Cl.
A61B 3/09 (2006.01)
A61B 3/028 (2006.01)
A61B 3/08 (2006.01)
A61B 3/00 (2006.01)

(52) U.S. Cl.
CPC ............... *A61B 3/09* (2013.01); *A61B 3/103* (2013.01); *G02C 7/02* (2013.01); *G02C 2202/24* (2013.01)

(58) Field of Classification Search
CPC .......... A61B 3/107; A61B 3/024; G02C 7/02; G02C 7/027; G02C 7/04; G02C 2202/24
USPC .......... 351/201, 205, 210, 212, 222, 159.74, 351/159.79, 159.78, 159.76, 159.01
See application file for complete search history.

(56) References Cited

OTHER PUBLICATIONS

Leung et al. "Progression of Myopia in Hong Kong Chinese schoolchildren is slowed by wearing progressive lenses", Optometry and Vision Science, vol. 76, No. 6, Jun. 1999, pp. 346-354.
Gwiazda et al. "A randomized clinical trial of progressive addition lenses versus single vision lenses on the progression of myopia in children", Investigative Ophthalmology & Visual Science, vol. 44, No. 4, Apr. 2003, pp. 1492-1500.
Hastings Edwards et al. "The Hong Kong progressive lens myopia control study: study design and main findings", Investigative Ophthalmology & Visual Science, vol. 43, No. 9, Sep. 2002, pp. 2852-2858.
Jiang et al. "Optimal dioptric value of near addition lenses intended to slow myopic progression", Optometry and Vision Science, vol. 85, No. 11, Nov. 2008, pp. 1100-1105.

* cited by examiner

METHOD AND SYSTEM FOR DETERMINING PERSONALIZED NEAR ADDITION VALUE, LENS WITH SUCH ADDITION

RELATED APPLICATIONS

This is a U.S. national stage application under 35 USC § 371 of International application No. PCT/CN2014/073061 filed on Mar. 7, 2014, the entire content of which is hereby incorporated by reference.

FIELD OF THE INVENTION

The present invention relates generally to methods and systems for determining personalized near addition value for non-presbyopic people, especially children and young adults, and also the present invention relates to ophthalmic lenses with near addition value determined thereby.

BACKGROUND OF THE INVENTION

Human eyes are the organs of vision. They sense the light and convert it into electro-chemical impulses in neurons, so as to create a vivid vision in the brain. The eye (eyeball) is only one inch in diameter but a complex optical system. It collects light from the surrounding environment, regulates its intensity through the pupil, focuses it through an adjustable assembly of lenses, and forms an image on the retina.

However, according to some studies, in the modern world about 80% of the population suffers from different vision impairments/disorders caused by refractive error, wherein an optical state of the eye in which the focus of the eye is incorrect causing blurred vision, includes myopia, hyperopia (far-sightedness or long-sightedness) and refractive astigmatism. Among these errors, myopia or the so-called near-sightedness becomes more and more prevalent. Particularly, myopia is the most common eye problem among children and young adults in many countries, especially in Asian countries, such as China, as education systems become more demanding, and electronic display devices become increasingly popular and prevalent.

In cases of myopia, the visual focus defect is such that distant objects (items in the scenery being viewed by the eye) appear blurred because their images are focused in front of the retina instead of on the retina. Myopia brings inconvenience to the people. In particular, people with relatively low degrees of myopia usually require an optical correction (spectacles or contact lenses) to allow them to drive a car or see the school blackboard, whereas those with high myopia also have an increased risk of developing blinding conditions such as retinal detachment and glaucoma.

Various classification systems have been described for myopia, and the following classification is commonly used by clinical entity, in which different myopia types are classified by their causes:

Simple myopia (also called school myopia) is usually caused by extensive vision stress such as long time reading, study, near works, and etc., and is far more common than any other type of myopia, which affects about 30% of population.

Pseudomyopia refers to an intermittent and temporary shift in refraction of the eye towards myopia, in which the focusing of light in front of the retina is due to overstimulation of the eyes' accommodative mechanism or ciliary spasm.

Degenerative myopia, also known as malignant, pathological, or progressive myopia, is characterized by marked fundus changes, such as posterior staphyloma, and associated with a high refractive error and subnormal visual acuity after correction.

Nocturnal myopia, also known as night or twilight myopia, is a condition in which the eye has a greater difficulty seeing in low-illumination areas, even though its daytime vision is normal.

Induced myopia, also known as acquired myopia, results from exposure to various pharmaceuticals or toxic chemicals, increases in glucose levels, nuclear sclerosis, oxygen toxicity (e.g., from diving or from oxygen and hyperbaric therapy) or other anomalous conditions.

Simple myopia, degenerative myopia, and induced myopia are called physiological myopia with structure defects on the eyes, contrary to pseudomyopia, which can be restored if treated promptly, especially for young adults and children.

In the art, there are several ways to correct myopia, among which the following three methods are most popular:

1) To provide ophthalmic lenses (spectacles and contact lenses) with proper negative or minus diopters which optically change the position of the focus of the visual image so the image is lying on the retina;
2) To conduct refractive surgery on the eyeballs so as to physically decrease the optical power of the cornea or of the crystalline lens and thus let the light focus on the retina and restore a clear vision; and
3) To prescribe pharmacological agents such as atropine or pirenzipine especially for pseudomyopia, in which the focusing of light in front of the retina is due to a transient spasm of the ciliary muscle causing an increase in the refractive power of the eye.

However, the first two methods do little to slow or stop the progression of myopia, and, according to at least some research findings, they may even actually promote the progression of myopia. As for the third method, the potential disadvantages associated with the long-term use of such pharmacological substances may render such modalities unattractive.

Therefore, methods and systems for inhibiting myopia, especially at an earlier stage, have been widely studied. People found that both genetic and environmental (intensive and excessive near work) factors may contribute to the cause and the development of myopia, and most studies show that the environmental factor plays a predominant role. It is proven that excessive near work needs prolonged muscular effort of focusing the eyes at near (accommodation) which results in a lag of accommodation (insufficient accommodation) and hyperopic retinal defocus (behind the retina), which may change the structure of the eye, such as an increase of axial length of the eyeball, and thus permanently result in the physiological myopia and its progression.

Furthermore, there is one widely acknowledged theory, lag and lead of accommodation theory, for explaining the relationship between accommodation and the cause of myopia. It is known that when subjects look at a given object, through the mechanism of accommodation, the curvature of the crystalline lens is changed and therefore the power of the eye, allowing generally a clear vision of the object. However, due in particular to the depth of field of the eye and the tolerance to blur of the human visual system, the amount of accommodation is most of the time not the theoretical value, for example theoretically, for an object at 40 cm, the accommodation value should be 2.5 diopters. When the accommodation is less than the calculated accommodation, it is called a lag of accommodation. If the accommodation is higher than what is theoretically needed, it's called a lead of accommodation. It is believed that the lag of accommodation (insufficient accommodation) may induce myopia progression through retinal hyperopic defocus.

On the basis of this theory, studies have found lenses with plus addition could provide clear vision with less accommodation during near viewing, thereby preventing myopia or slowing the progression of myopia, since additions or near additions reduce the lag of accommodation (insufficient accommodation).

In this regard, standard near additions have been used for decades to slow myopia progression or to prevent its onset especially for children and young adults.

In some studies (Leung & Brown, 1999; Edwards et al., 2002; Gwiazda et al, 2003; etc.), it is shown that the success of the standard near additions is limited considering all children. In some specific subgroups of children, their effect was significant, for example near esophores with high lags of accommodation. Moreover, even in those subgroups, fixed additions had a better efficacy in some children compared to others. One possible explanation for the lack of efficacy in some children compared to others is that the standard addition value is not adapted for each child, especially considering their effect on the child's binocular vision. Therefore, if the addition is too high, the child will not use it. If the addition is too low, it will have insufficient impact on the lag of accommodation and its efficacy will also be reduced.

U.S. Pat. No. 8,511,819 B2 also describes a method for preventing the onset of myopia, consisting of prescribing a pair of glasses with a standard addition of +2.00 diopters. However, the addition value is fixed and its efficacy should therefore be limited as described above.

However, the above studies mainly consider the accommodative response only and are silent about the binocular conditions, such as convergence responses, like near phoria compensation, which may lead to discomfort.

To this end, some scientific articles have investigated methods to determine the addition value by considering both accommodative and convergence responses for binocular vision, which either strongly reduces the lag of accommodation or brings the near phoria into a "normal" domain. Jiang et al. (2008) suggested two formulas. One based on one lag of accommodation measurement and another based on one phoria measurement to determine the optimal addition value to slow myopia progression.

However, it is still not clear if such addition value is well tolerated by the child in terms of binocular vision, especially in terms of motor and sensory fusion, or if it is high enough to have an effect on myopia progression.

Therefore, none of the prior art provides a comprehensive, simple and effective method or system to determine a personalized near addition value suited for myopes or non-presbyopes especially for children or young adults.

SUMMARY OF THE INVENTION

An object of the present invention is to provide a method for determining personalized near addition value for non-presbyopes, including myopia and emmetropia, so as to overcome the disadvantages mentioned, and provide an improved and customized near addition value for subjects, especially for children and young adults, which on the one hand more effectively prevents and controls the myopia, and on the other hand provides more comfortable binocular vision.

One aspect of the invention is directed to a method that comprises the following steps:
measuring fusional amplitudes and phoria with at least one addition value, for example null, on both eyes of a person at a working distance;
finding a mathematical function that predicts the change of a pair of fusional amplitudes and phoria as a function of addition value based on the addition value and the measured fusional amplitudes and phoria; and
determining the near addition value according to a suitable relationship between the pair of fusional amplitudes and phoria on the mathematical function.

Within the scope of the present patent application, fusional amplitudes are defined as the maximum amount of horizontal prism (either base in or base out) placed in front of the eyes that still can be fused (produce a single perceived image). Practically, increasing amounts of prisms are placed in front of the eyes until the subject declares seeing double. The prisms could be induced, for example, using a prism bar or a Risley variable prism.

The addition value thus determined by the present invention is the highest addition value that satisfies a binocular vision comfort criterion (e.g., Sheard Criterion or Percival Criterion), reducing the lag of accommodation while not inducing any lead of accommodation (over-accommodation). Such near addition value can be tolerated by the wearer, especially by children and young adults.

According to an embodiment of the invention, the pair of fusional amplitudes and phoria is represented by the absolute value of the ratio between the fusional amplitudes and the phoria. In addition, the suitable relationship between the pair of fusional amplitudes and phoria is when the absolute value of the ratio is comprised between 1.5 and 2.5, preferentially between 1.9 and 2.1, ideally equal to 2.

According to another embodiment of the invention, the mathematical function is an inverse proportional function $|FA/Ph|=a/(b \times ADD+c)$, or a linear regression function $|FA/Ph|=a \times ADD+b$, where $|FA/Ph|$ is the absolute value of the ratio between the fusional amplitudes and the phoria, ADD is the addition value corresponding to the fusional amplitudes and the phoria, and a, b, c are constants optimized for each subject.

Furthermore, a square root of the coefficient of determination of the mathematical function is larger than 0.9, preferentially larger than 0.95.

Alternatively, the fusional amplitudes and phoria are measured for near vision at the working distance for children or young adults aged between 2 to 25 years.

Alternatively, the working distance is a natural working distance defined for each wearer, especially children or young adults, for example between 20 cm to 40 cm.

Additionally, the fusional amplitudes are measured for only one addition value, and the phoria is measured for more than one addition value.

In addition, the near addition value is fine-tuned by being rounded up or down to the closest 0.25 diopters value. On the one hand, the method can further comprise a step of measuring a lag of accommodation with the fine-tuned near additional value addition at the near work distance, and if a result is a lead of accommodation, the near addition is decreased until a lag or precise focus is reached. On the other hand, if the fine-tuned near addition value is lower than a minimum positive constant ADD_min, the constant ADD_min is determined as the final near addition value, or if the fine-tuned near addition value is higher than a maximum positive constant ADD_max, the constant ADD_max is determined as the final near addition value.

A second aspect of the invention provides a lens controlling myopia progression or preventing the onset of myopia, wherein the near vision addition is designed according to the method mentioned above.

Alternatively, the lens is a contact lens or spectacle lens, for example, single vision glass, bifocal spectacle lens, or progressive spectacle lens.

Advantageously, the lens is worn for prolonged periods for near work time, for example over six months.

A third aspect of the invention provides a system for determining personalized near addition value for non-presbyopes comprising:

means for accepting the input of the measured fusional amplitudes and phoria with at least one addition value on a subject's both eyes;

means for calculating a mathematical function that predicts the change of a pair of fusional amplitudes and phoria as a function of addition value based on the addition value and the measured fusional amplitudes and phoria; and means for determining the near addition value according to a suitable relationship between the pair of fusional amplitudes and phoria on the mathematical function.

A detailed possible embodiment of such a system is described hereinafter.

A fourth aspect of the invention provides a computer program product for a data processing device, the computer program product comprising a set of instructions which, when loaded into the data processing device, causes the data processing device to perform at least one of the steps, for example all of the steps, of the method according to the invention.

Another aspect of the invention provides a computer-readable medium carrying one or more set of instructions of a computer program product of the invention.

It is known that the higher the addition, the better the effect can be obtained on myopia progression. However, if the addition is too high, the subjects may not be comfortable with this addition and will not use it, which will not obtain ideal myopia control effect or even result in a negative effect. This is a common problem in the art. In this regard, the present invention provides an advanced solution to such a problem by customizing near addition value on the basis of binocular vision condition through a unique method and system. Therefore, the present invention provides the highest addition value that can be tolerated by the subjects, especially children and young adults.

Due to the abovementioned method and system, the efficacy of the personalized addition determined by the present invention is improved compared to a standard addition. In particular, the present method and system is especially efficient for exophoric children, for whom standard additions do not work well.

BRIEF DESCRIPTION OF THE DRAWINGS

Other features and advantages of the invention will be apparent from the following description, with reference to the attached drawings in which.

DETAILED DESCRIPTION OF THE DRAWINGS

Figure 1:
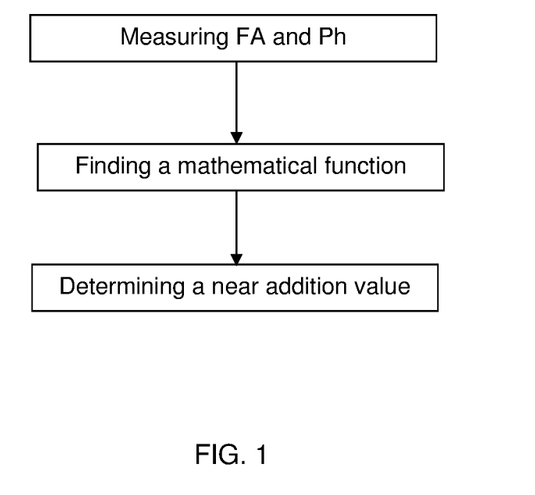
FIG. 1 is a flowchart showing the main steps of the method according to an embodiment of the present invention.

FIG. 1 shows the main steps of a method for determining personalized near addition value for non-presbyopes according to one embodiment of the present invention. In general, the method comprises the following steps:

measuring fusional amplitudes FA and phoria Ph with at least one addition value, which could be null, on both eyes of a subject, who will wear a pair of lenses prescribed according to the present method, at a working distance;

finding a mathematical function that predicts the change of a pair of fusional amplitudes FA and phoria Ph as a function of addition value ADD based on the addition value and the measured fusional amplitudes FA and phoria Ph; and determining the near addition value according to a suitable relationship between the pair of fusional amplitudes FA and phoria Ph on the mathematical function.

Advantageously, the pair of fusional amplitudes FA and phoria Ph is represented by the absolute value of the ratio between the fusional amplitudes FA and the phoria Ph, the ratio |FA/Ph|. In addition, the suitable relationship between the pair of fusional amplitudes FA and phoria Ph is when the ratio |FA/Ph| comprised between 1.5 and 2.5, preferentially between 1.9 and 2.1, ideally equal to 2.

Furthermore, the mathematical function is for example an inverse proportional function $|FA/Ph|=a/(b \times ADD+c)$, where a, b, and c are constants optimized for each subject, or a linear regression function $|FA/Ph|=a \times ADD+b$, where a and b are constants optimized for each subject, which are discussed in the examples hereinafter. In addition, in case of a linear regression, the ratio |FA/Ph| for a null addition could be excluded for the fit.

In these examples, the fusional amplitudes FA and phoria Ph are measured for near vision at the working distance for subjects, especially children or young adults aged between 2 to 25 years, and the working distance is a natural working distance defined for each child or young adult, for example between 20 cm to 40 cm. In addition, the fusional amplitudes FA are measured Base Out when the phoria Ph measured with addition is exophoria, and the fusional amplitudes FA are measured Base In when the phoria Ph measured with addition is esophoria. The fusional amplitudes FA is considered negative when Base In and positive when Base out, and the phoria Ph is considered negative when exophoria and positive when esophoria.

Moreover, in these examples, the near addition value is fine-tuned by being rounded up or down to the closest 0.25 diopters value.

Furthermore, the measurements of accommodative response (lag of accommodation), fusional amplitudes FA, and phoria Ph are conducted through conventional methods and apparatus.

Also, the additions obtained by these examples are usually the same for both eyes, as accommodation is the same in both eyes. Therefore, one addition refers to both lenses, in order to have one pair of lenses.

EXAMPLE 1

Fast Method with Progressive Myopia

A child with progressive myopia is examined to determine the best addition value in order to prescribe a pair of progressive lenses to slow down its myopia progression.

Its base-out fusional amplitude $FA_0$ without addition (0.00 D) is measured at 33 cm using a phoropter and Risley variable prisms.

$FA_0$=23 pr.D (measured without addition)
Phoria Ph is measured at 33 cm with the following additions, using a modified Thorington technique:
+1.00 D : $Ph_{+1.00}$=−10 pr.D, $|FA_0/Ph_{+1.00}|$=2.3
+2.00 D : $Ph_{+2.00}$=−14 pr.D, $|FA_0/Ph_{+2.00}|$=1.64

Figure 2:
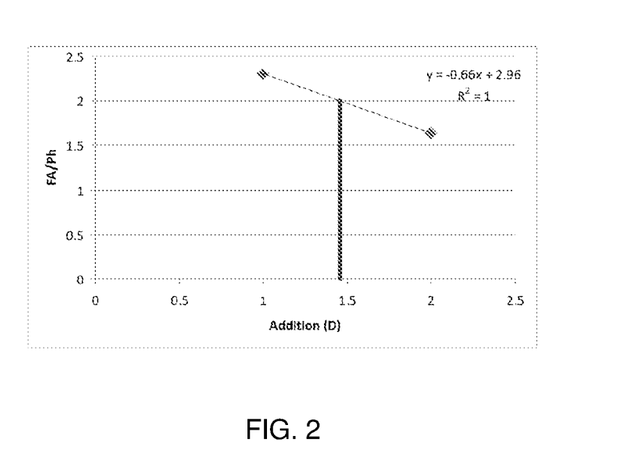
FIG. 2 is a graph showing a function obtained by a first example according to the present invention.

The ratio $|FA_0/Ph|$ is plotted as a function of the addition value and fitted with a linear regression function, see FIG. 2. The addition value is determined by the equation as the value that provides a $|FA_0/Ph|$ ratio equal to 2 and rounded up to the closest 0.25 value.

The ideal addition value is 1.45 D. Therefore, a pair of progressive addition lenses (PAL) with an addition of +1.50 D is prescribed.

EXAMPLE 2

Precise Method with Pre-myopia and Personalized Distance

An emmetropic child, suspected to become myopic (pre-myopia), is examined in order to prescribe a pair of reading glasses to be worn during near work to prevent the onset of myopia.

The usual working distance of the child is measured with a ruler while it reads a comic book: 25 cm.

The child's base-out fusional amplitude and phoria are measured at usual working distance (25 cm, measured above) with the following additions:
Without addition (0.00 D) : $FA_0$=16 pr.D, $Ph_0$=−3.5 pr.D, $|FA_0/Ph_0|$1=4.57
+1.00 D : $FA_{+1.00}$=15 pr.D, $Ph_{+1.00}$=−8 pr.D, $|FA_{+1.00}/Ph_{+1.00}|$=1.88
+1.50 D : $FA_{+1.50}$=15 pr.D, $Ph_{+1.50}$=−9 pr.D, $|FA_{+1.50}/Ph_{+1.50}|$=1.67
+2.00 D : $FA_{+2.00}$=15 pr.D, $Ph_{+2.00}$=−12 pr.D, $|FA_{+2.00}/Ph_{+2.00}|$=1.25
+2.50 D : $FA_{+2.50}$=15 pr.D, $Ph_{+2.50}$=−13.5 pr.D, $|FA_{+2.50}/Ph_{+2.50}|$=1.11
+3.00 D : $FA_{+3.00}$=14 pr.D, $Ph_{+3.00}$=−16 pr.D, $|FA_{+3.00}/Ph_{+3.00}|$=0.88

Figure 3:
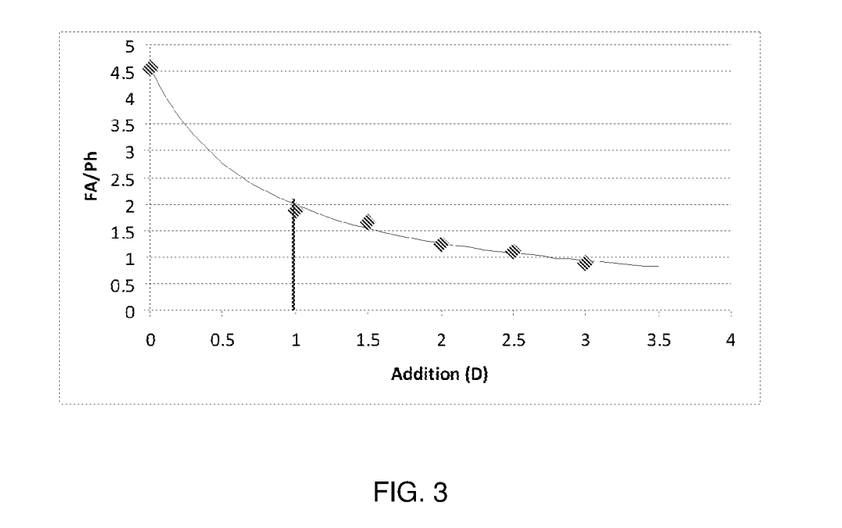
FIG. 3 is a graph showing a function obtained by a second example according to the present invention.

The ratio $|FA/Ph|$ is plotted as a function of the addition value and fitted with a $|FA/Ph|=a/(b \times ADD+c)$ function, see FIG. 3. The result is a=14.47; b=4.14; c=3.17. The addition value is determined by the equation as the value that provides a ratio equal to 2 and rounded up to the closest 0.25 value.

The theoretical addition value is 0.98 D. The lag of accommodation is then measured at 25 cm with a 1.00 D addition by means of a Grand Seiko WAM 5500 open field auto-refractor. A lag of 1.23 D is measured (no lead). The accommodation measurement leaves the addition value unchanged (in case of a measured lead of accommodation, the addition value would have been decreased until a lag or zero accommodation error is reached).

Therefore, a pair of near single vision lenses with an addition (also the power of the lenses) of +1.00 D is prescribed.

EXAMPLE 3

Precise Method and Progressing Myopia

A child with progressive myopia is examined to determine the best addition value in order to prescribe a pair of bifocal lenses to slow down its myopia progression. Bifocals are preferred to progressive lenses in this case, as the child spends a lot of time reading and needs good wide visual fields. Moreover, two pairs of spectacles were considered too complicated to manage by the parents.

The child's base-out fusional amplitude and phoria are measured at 33 cm with the following additions:
Without addition (0.00 D) : $FA_0$=19 pr.D, $Ph_0$=−1 pr.D, $|FA_0/Ph_0|$=19
+1.00 D : $FA_{+1.00}$=19 pr.D, $Ph_{+1.00}$=−4.5 pr.D, $|FA_{+1.00}/Ph_{+1.00}|$=4.22
+1.50 D : $FA_{+1.50}$=20 pr.D, $Ph_{+1.50}$=−6.5 pr.D, $|FA_{+1.50}/Ph_{+1.50}|$=3.08
+2.00 D : $FA_{+2.00}$=18 pr.D, $Ph_{+2.00}$=−8.5 pr.D, $|FA_{+2.00}/Ph_{+2.00}|$=2.12
+2.50 D : $FA_{+2.50}$=19 pr.D, $Ph_{+2.50}$=−11 pr.D, $|FA_{+2.50}/Ph_{+2.50}|$=1.73
+3.00 D : $FA_{+3.00}$=19 pr.D, $Ph_{+3.00}$=−12.5 pr.D, $|FA_{+3.00}/Ph_{+3.00}|$=1.52

Figure 4:
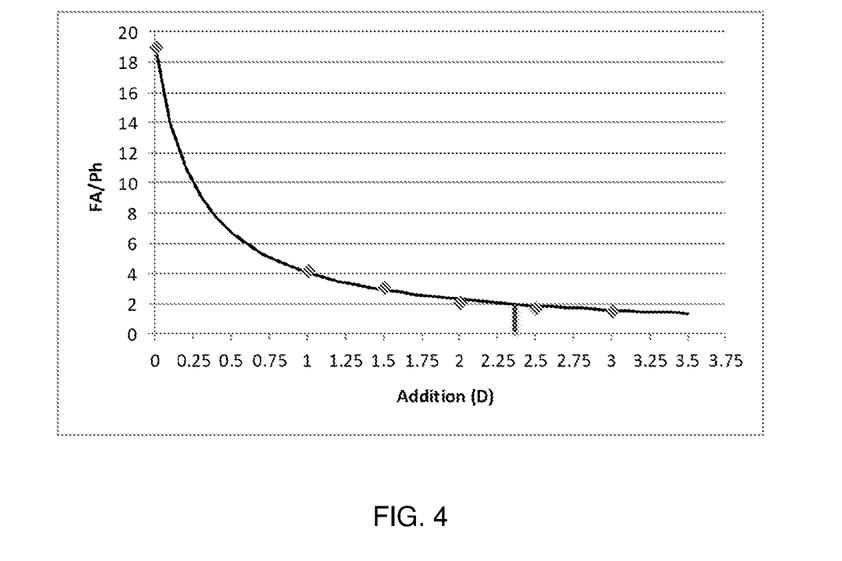
FIG. 4 is a graph showing a function obtained by a third example according to the present invention.

The ratio $|FA/Ph|$ is plotted as a function of the addition value and fitted with a $|FA/Ph|=a/(b \times ADD+c)$ function, see FIG. 4. The result is a=2.87; b=−0.55; c=−0.15. The addition value is determined by the equation as the value that provides a ratio equal to 2 and rounded up to the upper 0.25 value.

The theoretical addition value is 2.33 D. The lag of accommodation is then measured at 33 cm with a 2.50 D addition by means of a Grand Seiko WAM 5500 open field auto-refractor. A lead of 0.28 D is measured: the addition is too high. The lag of accommodation is then measured with an addition of +2.25D. A lag of 0.05D is measured (no lead).

Therefore, the addition of +2.25 is adopted, and a pair of bifocal lenses with an addition of +2.25 D is prescribed.

EXAMPLE 4

Myopic Child with High Near Esophoria

This child is similar to the one in example 1, except that it has a high near esophoria. Therefore, Base-In FA are measured instead of Base out.

The child's base-in fusional amplitude and phoria are measured at 33 cm with the following additions:
Without addition (0.00 D) : $FA_0$=−15 pr.D, $Ph_0$=+15.5 pr.D, $|FA_0/Ph_0|$=0.97
+1.00 D : $FA_{+1.00}$=−15 pr.D, $Ph_{+1.00}$=+12 pr.D, $|FA_{+1.00}/Ph_{+1.00}|$=1.25
+1.50 D : $FA_{+1.50}$=−14 pr.D, $Ph_{+1.50}$=+10.5 pr.D, $|FA_{+1.50}/Ph_{+1.50}|$=1.33
+2.00 D : $FA_{+2.00}$=−15 pr.D, $Ph_{+2.00}$=+8.5 pr.D, $|FA_{+2.00}/Ph_{+2.00}|$=1.76
+2.50 D : $FA_{+2.50}$=−16 pr.D, $Ph_{+2.50}$=+7 pr.D, $|FA_{+2.50}/Ph_{+2.50}|$=2.29
+3.00 D : $FA_{+3.00}$=−15 pr.D, $Ph_{+3.00}$=+5.5 pr.D, $|FA_{+3.00}/Ph_{+3.00}|$=2.73

Figure 5:
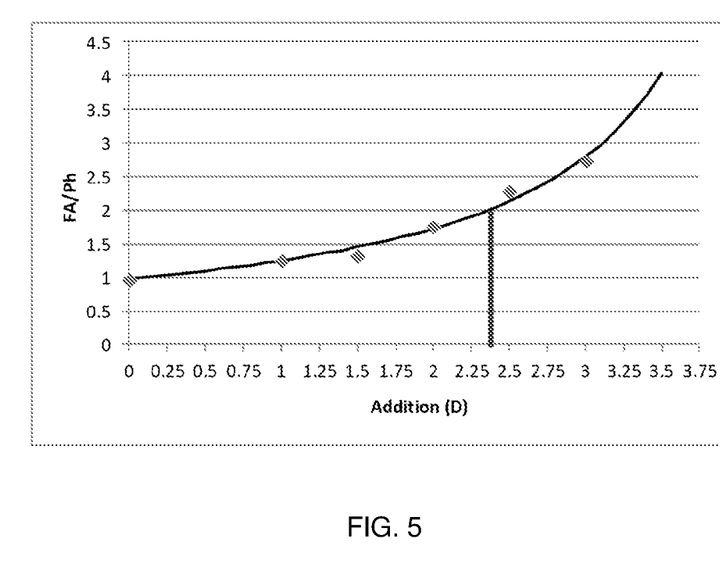
FIG. 5 is a graph showing a function obtained by a fourth example according to the present invention.

The ratio |FA/Ph| is plotted as a function of the addition value and fitted with a |FA/Ph|=a/(b×ADD+c) function, see figures. The result is a=33.10; b=−7.28; c=33.70. The addition value is determined by the equation as the value that provides a ratio equal to 2 and rounded up to the upper 0.25 value.

The theoretical addition value is 2.36 D. The accommodative response is then measured at 33 cm with a 2.50 D addition by means of a Grand Seiko WAM 5500 open field auto-refractor. A lag of 0.42 D is measured (no lead). The accommodation measurement leaves the addition value unchanged.

Therefore, a pair of progressive lenses with an addition of +2.50 D is prescribed.

EXAMPLE 5

Pilot Experiment on 30 Children

Figure 6:
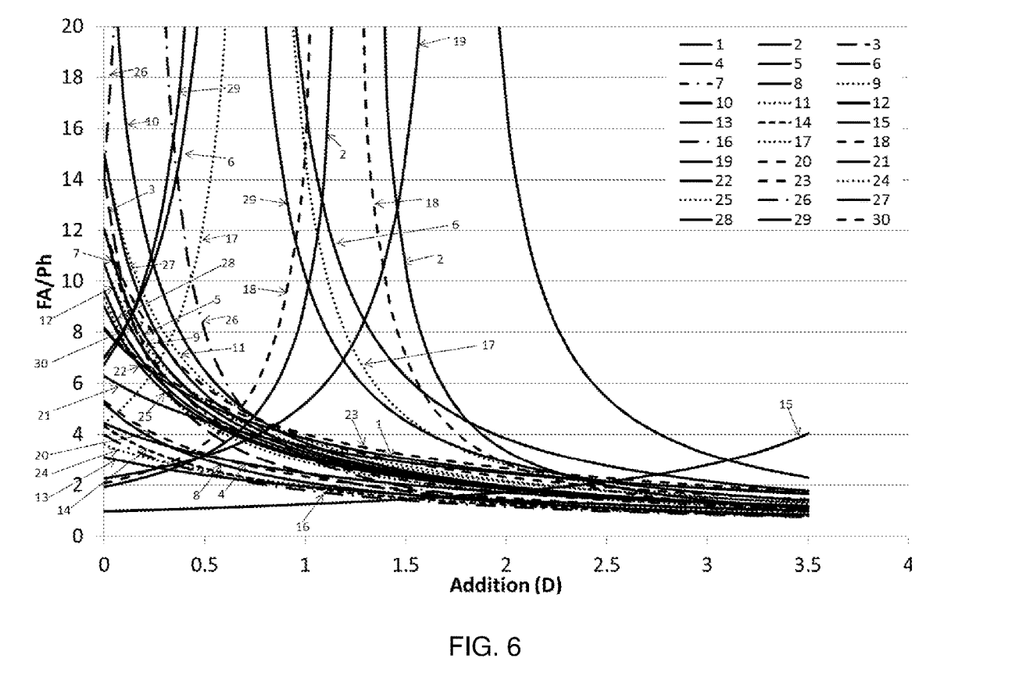
FIG. 6 is a graph showing thirty functions obtained by a fifth example according to the present invention.

In a pilot experiment carried out by the applicant, FA, Ph, and accommodation in 30 children, aged 8 to 10 years old, have been measured. Then the ratio |FA/Ph| is plotted as a function of addition value and fitted with a |FA/Ph|=a/(b× ADD+c) function for each child (subject), see FIG. 6, wherein the square root R of the coefficient of determination for each subject is perfectly near 1, particularly larger than 0.9, preferentially larger than 0.95. On the basis of the abovementioned method, we obtain the results of a, b, and c for each subject, the addition values (ADD) that are determined by the equation as the value that provides a ratio equal to 2 and rounded up to the upper 0.25 value, as well as the addition values (ADD, Lag=0) determined by a lag of accommodation=0, as shown in the table below.

small difference), showing that the lag=0 method prescribes additions that are too high and will therefore not be well tolerated by the subjects, especially children and young adults, whereas the near addition obtained by the claimed method provides more comfortable binocular vision, while still suitable for near addition prescription for preventing myopia or slowing myopia progression.

In addition, it seems unnecessary to measure systematically the lag of accommodation to prescribe the personalized addition since the results have shown that, the addition determined by the formula |FA/Ph|=2 is nearly always lower than the value that provides a lag of accommodation=0. Therefore, the method can be simplified and limited to FA and Ph measurement only in most cases.

Furthermore, it is also shown that FA did not vary much with the addition. In this case, the fusional amplitudes FA could be measured for only one addition value, which increases the determination speed and makes the whole process less tiring for the subject.

Advantageously, if the fine-tuned near addition value is lower than a minimum positive constant ADD_min, for example 0.50 D or 0.75 D, the constant ADD_min is determined as the final near addition value, and if the fine-tuned near addition value is higher than a maximum positive constant ADD_max, for example 3.00 D or 3.50 D, the constant ADD_max is determined as the final near addition value.

In order to increase the speed of the prescription method, a specific computer program software in which the method is implemented can guide the practitioner by suggesting which lens to use and by calculating the final addition based on a complex mathematical data fit. In a more sophisticated

|  | a | b | c | ADD (theoretical/prescribed) | R | ADD, Lag = 0 |
|---|---|---|---|---|---|---|
| Subject 1 | 8.27 | 1.13 | 1.02 | 2.50/2.75 | 0.981 | 3.00/3.25 |
| Subject 2 | −1299.99 | 528.87 | −670.01 | 2.25/2.50 | 0.933 | 2.75/3.00 |
| Subject 3 | 14.81 | 4.90 | 1.06 | 1.25/1.50 | 0.999 | 2.00/2.25 |
| Subject 4 | 2.41 | 0.43 | 0.54 | 1.50/1.75 | 0.999 | 2.75/3.00 |
| Subject 5 | 0.68 | −0.15 | −0.06 | 1.75/2.00 | 0.999 | 3.00/3.25 |
| Subject 6 | 3.44 | 0.69 | −0.49 | 3.00/3.25 | 0.998 | 3.50/3.75 |
| Subject 7 | 0.94 | −0.23 | −0.08 | 1.50/1.75 | 0.999 | 1.50/1.75 |
| Subject 8 | 9.45 | 2.65 | 1.81 | 1.00/1.25 | 0.998 | 3.50/3.75 |
| Subject 9 | 0.44 | −0.08 | −0.04 | 2.00/2.25 | 0.998 | 2.25/2.50 |
| Subject 10 | 22.07 | 5.22 | 0.79 | 1.75/2.00 | 0.999 | 2.25/2.50 |
| Subject 11 | 0.34 | −0.07 | −0.02 | 2.00/2.25 | 0.999 | 2.25/2.50 |
| Subject 12 | 12.08 | 2.63 | 1.13 | 1.75/2.00 | 0.999 | 3.50/3.75 |
| Subject 13 | 7.72 | 1.48 | 2.48 | 0.75/1.00 | 0.996 | 3.50/3.75 |
| Subject 14 | 0.78 | 0.23 | 0.18 | 0.75/1.00 | 0.994 | 2.75/3.00 |
| Subject 15 | 33.10 | −7.29 | 33.70 | 2.25/2.50 | 0.990 | 3.50/3.75 |
| Subject 16 | 0.47 | 0.14 | 0.12 | 0.75/1.00 | 0.998 | 2.00/2.25 |
| Subject 17 | −1.13 | −0.33 | 0.25 | 2.25/2.50 | 0.999 | 2.25/2.50 |
| Subject 18 | −93.79 | 38.93 | −45.12 | 2.25/2.50 | 0.981 | 3.50/3.75 |
| Subject 19 | 10235.69 | −2562.97 | 4525.03 | 3.75/4.00 | 0.999 | 3.50/3.75 |
| Subject 20 | 18.50 | 4.43 | 3.48 | 1.25/1.50 | 0.997 | 3.25/3.50 |
| Subject 21 | 340.36 | −41.93 | −54.16 | 2.75/3.00 | 0.908 | 3.00/3.25 |
| Subject 22 | 1138.58 | 246.09 | 126.43 | 1.75/2.00 | 0.999 | 2.50/2.75 |
| Subject 23 | 298.62 | 37.73 | 36.53 | 2.75/3.00 | 0.963 | 2.75/3.00 |
| Subject 24 | 28.41 | 6.35 | 7.90 | 0.75/1.00 | 0.999 | 2.25/2.50 |
| Subject 25 | 78.33 | −18.49 | −8.40 | 1.50/1.75 | 0.999 | 2.25/2.50 |
| Subject 26 | 9340.37 | 3656.07 | −667.01 | 1.25/1.50 | 0.999 | 2.75/3.00 |
| Subject 27 | 30.35 | −6.81 | −2.02 | 1.75/2.00 | 0.999 | 2.25/2.50 |
| Subject 28 | 136.98 | −29.79 | −14.25 | 1.75/2.00 | 0.999 | 2.75/3.00 |
| Subject 29 | −1006128.40 | −247641.77 | 149348.98 | 2.50/2.75 | 0.999 | 3.75/4.00 |
| Subject 30 | 5.76 | −1.00 | −0.48 | 2.25/2.50 | 0.999 | 3.00/3.25 |

From the results shown in the table, it is obvious that the addition values obtained by the present method are always lower than the ones determined by lag=0 (except for 1 child, version, the program could also directly control the phoropter or even a specific machine whose sole purpose is to determine the personalized addition value described above.

For example, such computer program software proceeds in the following steps:
1. Input of Ph and FA (Ph0 and FA0), measured by the practitioner for a starting addition value ADD0. ADD0 could be for example equal to zero.
2. Input of Phoria (Ph1) (and optionally Fusional Amplitude FA1) measured by a first addition value ADD1 determined by the software, based on the average or median of the previous addition values previously prescribed. For first patients, this value can be arbitrarily set at +1.50 D for example.
3. If (|FA/Ph1|−2) <k1 (k1 is a constant, for example 0.1), the addition value ADD1 is prescribed.
4. Calculation of the next addition value ADD2 to be tested based on Ph1 and FA: if |FA/Ph1|>2 and phoria is <0, increase addition; if |FA/Ph1|<2 and phoria is <0, decrease addition. In case of phoria >0, proceed in the opposite way. The amount of decrease or increase |Δ| is a function of Ph0, Ph1, FA and ADD1, so that the theoretical phoria measurement Ph2 with ADD2 theoretically results in a ratio |FA/Ph2|=2, based on the linear equation linking |FA/Ph0| and |FA/Ph1|.
5. The Phoria Ph2 is measured with the above addition value ADD2.
6. If (|FA/Ph2|−2) <k2 (k2 is a constant, for example 0.1), the program stops, otherwise step 4 is repeated, using the 2 phoria values for which the ratios |FA/Ph| are the closest to 2.
7. The addition is calculated based on a mathematical function that fits all available points |FA/Ph| (as in the previous prescription method). Based on this function, the theoretical addition ADD_th value that provides a |FA/Ph| ratio of 2 is determined.
8. The prescribed addition value is rounded up to the closest 0.25 D value to ADD_th.

Figure 7:
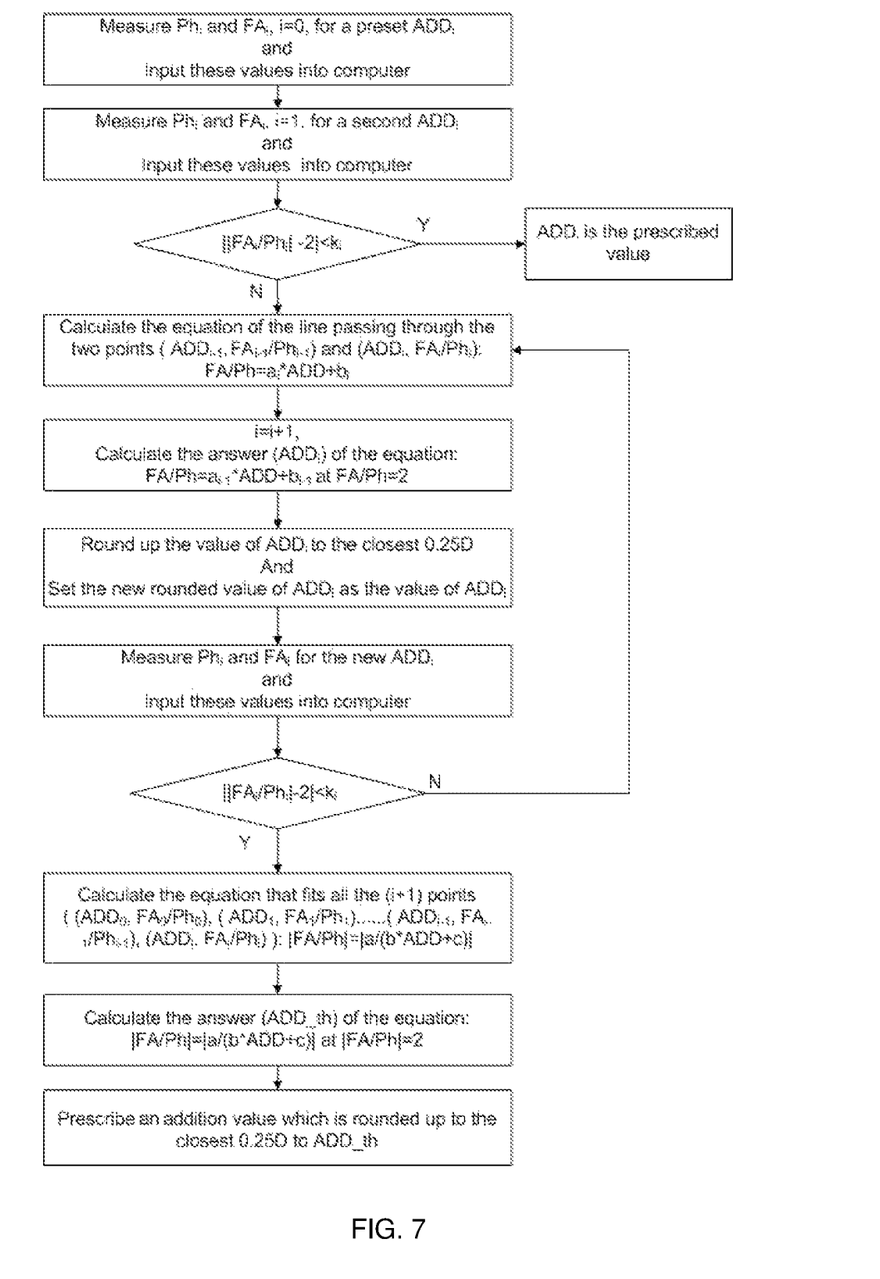
FIG. 7 is a flowchart showing the major steps of one embodiment of a program according to the method of present invention.

Referring to FIG. 7, a detailed example of determining near addition value according to the claimed method by a program is as follows.
1. Ph0 and FA0 are measured without addition. The child is exophoric (Ph0=−1Δ), therefore FA0 is measured for Base Out (FA0=19 ΔBI). |FA0/Ph0|=19
2. Ph1 and FA1 are measured with +1.50D addition: |FA1/Ph1|=|20/−6.51|=3.08
|3.08−2|>k (0.1). As |FA1/Ph1|>2, addition value is increased by program. The value is determined by the equation of the line passing through the 2 points (0, 19) and (1.5, 3.08). Equation: |Fa/Ph|=−10.613ADD+19. The theoretical value solving this equation for |Fa/Ph|=2 is ADD=1.60. Therefore, addition ADD2=+1.75 is measured (Next 0.25D)
4. ADD2=+1.75, |FA2/Ph2|=|19/7.5|=2.53.
5. |2.53−2|>k(0.1), As |FA2/Ph2|>2, addition value is increased by program. The program calculates the equation of the line passing through the 2 points (1.5, 3.08) and (1.75, 2.53): |FA/Ph|=−2.2ADD+6.38. The theoretical value solving this equation for |FA/Ph|=2 is ADD=1.99. Therefore, addition ADD3=+2.00 is measured (next 0.25D).
6. ADD3=+2.00, |FA3/Ph3|=|18/8.5|=2.12.
7. |2.12−2|>k(0.1), As |FA3/Ph3|>2, addition value is increased by program. The program calculates the equation of the line passing through the two points (1.75, 2.53) and (2.00, 2.12): |FA/Ph|=−1.64ADD+5.4. The theoretical value solving this equation for FA/Ph=2 is ADD=2.07. Therefore, addition ADD4=+2.25 is measured (Next 0.25D).
8. ADD4=+2.25, |FA4/Ph4|=19/10=1.9.
9. |1.9−2|=k. The program stops.
10. Addition is calculated with 5 measured points FA/Ph and ADD 0 to 4, using the best fit of the equation |FA/Ph|=|a/(b×ADD+c)|. The result is ADDITION=2.28 for |FA/Ph|=2, a=66.16, b=−12.97, c=−3.48.

Therefore, the addition +2.25 D is prescribed (closest to 2.28).

Figure 8:
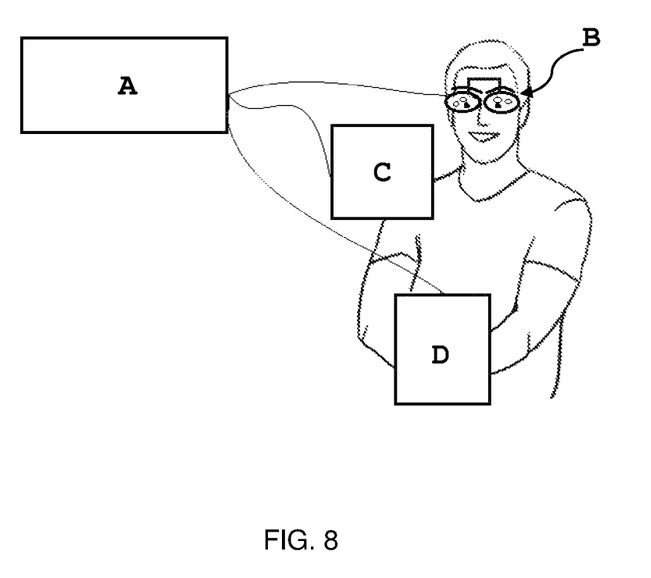
FIG. 8 is a diagram showing an example of a system for determining personalized near addition value for non-presbyopes.

FIG. 8 shows a possible implementation of a system for determining personalized near addition value for non-presbyopes, and the system comprises the following elements:

Computer A or similar data analyzing unit, which receives measurement information, for example FA and Ph, from the subject, analyzes the data, and calculates the final near additional value based on a program implementing the claimed method, for example a computer program mentioned above.

Automated lens device B, which is able to present the needed lenses (additions and prisms) for measuring at least fusional amplitudes and phoria in front of the subject's eyes. This device could be for example an automatic phoropter controlled by the computer A or any specific machine that can change lenses and prisms in front of a subject's eyes.

Display unit, which presents the targets for FA and Ph measurement at the chosen distance, for example a LCD screen or a tablet PC controlled by the computer A.

Response device D, for example a response pad, which is a mean to gather responses from the subject, for example, a game pad or tactile screen linked to the computer.

The system can also include a device for accommodation measurement, for example, an open field autorefractor (such as Grand Seiko WAM-5500) or a photorefractor such as PowerRef II (Plusoptix), controlled by the computer, to measure the lag of accommodation.

The computer A commands the automated lens device B to place the first addition lenses in front of the eyes of the subject. It will then display a FA test (for example a vertical line of letters) on the display unit C for FA measurement. Thereafter, the computer A commands the automated lens device B to increase binocularly and slowly the horizontal prism value in front of the eyes until the subject reports seeing double by pressing the response pad D. The computer A records the prism value when the subject presses the response pad D and records it as FA value.

The computer A commands then the automated lens device B to remove the horizontal prisms and to replace them with one Maddox rod placed in front of the right eye of the subject. It commands then to display a Modified Thorington phoria test on the display unit C. The subject then enters on the response pad D the value he reads on the phoria test. This value is recorded by the computer A value as Ph value. Then the Maddox rod is removed.

The computer A then determines the next addition value to be measured, based on a computer program according to the claimed method and the process is repeated until the final addition value is reached.

Alternatively, the system also comprises a device for accommodation measurement, and the accommodation value is then measured by the device for accommodation measurement with the addition value and analyzed by the computer A. The final addition value is adjusted according to the accommodation value (lag, lead or precise accommodation) as described above.

The scope of protection of the invention is not limited to the examples given hereinabove. The invention is embodied in each novel characteristic and each combination of characteristics, which includes every combination of any features which are stated in the claims, even if this feature or combination of features is not explicitly stated in the examples.

The invention claimed is:

1. A method for determining a personalized near addition value for non-presbyopes, comprising:
    measuring fusional amplitudes (FA) and phoria (Ph) with at least one addition value on both eyes of a subject at a working distance, the addition value being the same for both eyes, wherein the FA is measured via a lens device based on a maximum horizontal prism value that indicates when the subject begins to have diplopia by holding the at least one addition value constant and changing a horizontal prism value until the diplopia begins;
    based on an addition value (ADD) and the corresponding measured FA and Ph, plotting a mathematical function of a ratio |FA/Ph| vs. ADD; and
    determining, based on the plotted mathematical function, a near addition value for the subject that provides a value for the ratio |FA/Ph| being equal to set value, wherein
    the mathematical function is an inverse proportional function |FA/Ph|=a/(b.times.ADD+c), where a, b, c are constants optimized for each subject or is a linear regression function |FA/Ph|=d.times.ADD+e, where d and e are constants optimized for each subject, and the near addition value personalizes lenses for control of myopia of the subject.

2. The method according to claim 1, wherein the set value is between 1.5 and 2.5.

3. The method according to claim 1, wherein the FA and Ph are measured for near vision at the working distance for subjects aged between 2 to 25 years.

4. The method according to claim 3, wherein the FA is measured for only one addition value, and the Ph is measured for more than one addition value.

5. The method according to claim 1, wherein the working distance is a natural working distance defined for each subject.

6. The method according to claim 1, wherein the near addition value is fine-tuned by being rounded up or down to the closest 0.25 diopters value.

7. The method according to claim 6, wherein when the fine-tuned near addition value is lower than a minimum positive constant $ADD_{min}$, the constant $ADD_{min}$ is determined as the final near addition value, and when the fine-tuned near addition value is higher than a maximum positive constant $ADD_{max}$, the constant $ADD_{max}$ is determined as the final near addition value.

8. The method according to claim 1, further comprising measuring a lag of accommodation with the fine-tuned near addition value addition at the working distance, and when a result is a lead of accommodation, the near addition is decreased until a lag or precise focus is reached.

9. The method according to claim 1, wherein the set value is between 1.9 and 2.1.

10. The method according to claim 1, wherein the working distance is between 20 cm to 40 cm.

11. The method according to claim 1, wherein the near addition value is determined as the value that provides the ratio |FA/Ph| being equal to 2.0 and rounded up to the closest 0.25 value.

12. A lens for controlling myopia progression comprising:
    at least one surface with a personalized near addition value for a subject having progressing myopia, wherein
    the personalized near addition value is determined based on a plotted mathematical function between addition value (ADD) and the corresponding measured ratio of fusional amplitude (FA) and phoria (Ph) by determining a near addition value that provides a value for the ratio |FA/Ph| being equal to a set value,
    a measurement of the measured FA and Ph is made with at least one addition value on both eyes of the subject at a working distance, the addition value being the same for both eyes, the measured FA being measured, via a lens measurement device, based on a maximum horizontal prism value that indicates when the subject begins to have diplopia by holding the at least one addition value constant and changing a horizontal prism value until the diplopia begins, and
    the mathematical function is an inverse proportional function |FA/Ph|=a/(b.times.ADD+c), where a, b, c are constants optimized for each subject or is a linear regression function |FA/Ph|=d.times.ADD+e, where d and e are constants optimized for the subject.

13. The lens according to claim 12, wherein the lens is a contact lens or a spectacle tens.

14. The lens according to claim 12, wherein the lens is worn for prolonged periods of near work time.

15. A system for determining personalized near addition value for non-presbyopes comprising:
    a computer processor configured to perform:
        accepting an input of measured fusional amplitudes (FA) and phoria (Ph) with at least one addition value on a subject's both eyes, the addition value being the same for both eyes, the measured FA being measured, via a lens measurement device, based on a maximum horizontal prism value that indicates when the subject begins to have diplopia by holding the at least one addition value constant and changing a horizontal prism value until the diplopia begins;
        based on an addition value (ADD) and the corresponding measured FA and Ph, plotting a mathematical function of a ratio |FA/Ph| vs. ADD; and
        determining, based on the plotted mathematical function, a near addition value that provides a value for the ratio |FA/Ph| being equal to a set value, wherein
        the mathematical function is an inverse proportional function |FA/Ph|=a/(b.times.ADD+c), where a, b, c are constants optimized for each subject or is a linear regression function |FA/Ph|=d.times.ADD+e, where d and e are constants optimized for each subject, and the near addition value personalizes lenses for control of myopia of the subject.

* * * * *